(12) United States Patent
Hurley et al.

(10) Patent No.: US 9,487,546 B2
(45) Date of Patent: Nov. 8, 2016

(54) SOLID FORMS OF TENOFOVIR

(71) Applicant: Gilead Sciences, Inc., Foster City, CA (US)

(72) Inventors: Paul Bernard Hurley, Edmonton (CA); Olga Viktorovna Lapina, Newark, CA (US); Bing Shi, Redwood City, CA (US); Fang Wang, Foster City, CA (US); Zhi Xian Wang, Edmonton (CA); Jacqueline Ching-See Woo, Sherman Park (CA)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/593,556

(22) Filed: Jan. 9, 2015

(65) Prior Publication Data

US 2015/0197535 A1 Jul. 16, 2015

Related U.S. Application Data (60) Provisional application No. 61/927,617, filed on Jan. 15, 2014.

(51) Int. Cl.
*C07F 9/6561* (2006.01)

(52) U.S. Cl.
CPC ....... *C07F 9/65616* (2013.01); *C07B 2200/13* (2013.01)

(58) Field of Classification Search
CPC .................................................. C07F 9/65616
See application file for complete search history.

(56) References Cited

U.S. PATENT DOCUMENTS

| | | | |
|---|---|---|---|
| 5,922,695 A | 7/1999 | Arimilli et al. | |
| 5,935,946 A | 8/1999 | Munger, Jr. et al. | |
| 5,977,089 A | 11/1999 | Arimilli et al. | |
| 6,043,230 A | 3/2000 | Arimilli et al. | |
| 6,057,305 A | 5/2000 | Holy et al. | |
| RE38,333 E | 11/2003 | Arimilli et al. | |
| 7,390,791 B2 | 6/2008 | Becker et al. | |
| 7,803,788 B2 | 9/2010 | Becker et al. | |
| 8,592,397 B2 | 11/2013 | Dahl et al. | |
| 8,664,386 B2 | 3/2014 | Colby et al. | |
| 8,716,264 B2 | 5/2014 | Dahl et al. | |
| 8,754,065 B2 | 6/2014 | Liu et al. | |
| 9,029,534 B2 | 5/2015 | Colby et al. | |
| 2009/0286981 A1* | 11/2009 | Vasireddy et al. | 544/244 |
| 2013/0065856 A1* | 3/2013 | Liu et al. | 514/81 |

OTHER PUBLICATIONS

Gilead Sciences. "Gilead Sciences Begins Human Testing of Oral PMPA for treatment of HIV". (1997) pp. 1-2, <http://www.gilead.com/news/press-releases/1997/5/gilead-sciences-begins-human-testing-of-oral-pmpa-for-treatment-of-hiv>.*
Viral Infections: Medlineplus. NIH. (2016). Web. < https://www.nlm.nih.gov/medlineplus/viralinfections.html>.*
Tenofovir:MedlinePlus Drug Information. NIH. (2016). Web. < https://www.nlm.nih.gov/medlineplus/druginfo/meds/a602018.html>.*
Celum,Connie. Curr Opion Infect Dis 25(1) (2012) 51-57.*
International Search Report and Written Opinion for PCT/US2015/010831 dated Mar. 19, 2015.

* cited by examiner

*Primary Examiner* — Golam M M Shameem
*Assistant Examiner* — Laura Daniel
(74) *Attorney, Agent, or Firm* — Morrison & Foerster LLP (57) ABSTRACT

The present invention relates to solid forms of tenofovir and methods for preparation, use and isolation of such forms.

18 Claims, 5 Drawing Sheets

Figure 1. Experimental X-ray powder diffraction (XRPD) pattern of Form I

Figure 2. XRPD of Form IV

Figure 3. XRPD for Form VI

Figure 4. XRPD of Form IX

Figure 5. XRPD of Materials III, XIV, XVI, XVIII, and XIX.

SOLID FORMS OF TENOFOVIR

CROSS REFERENCE TO RELATED APPLICATIONS

This non-provisional application claims the benefit of Provisional Application No. 61/927,617, filed Jan. 15, 2014, which is incorporated herein by reference.

FIELD OF THE INVENTION

The present invention relates to solid forms of tenofovir and methods for preparation, use and isolation of such forms.

BACKGROUND OF THE INVENTION (R)-9-[2-(Phosphonomethoxy) propyl]adenine ("PMPA") or "tenofovir" can be used to make phosphonomethoxy nucleotides. Identifying new solid forms of tenofovir that could be used in a more efficient synthesis of phosphonomethoxy nucleotides is desirable.

SUMMARY OF THE INVENTION

The present invention provides crystalline forms of tenofovir, as well as uses and processes associated therewith.

Figure 1:
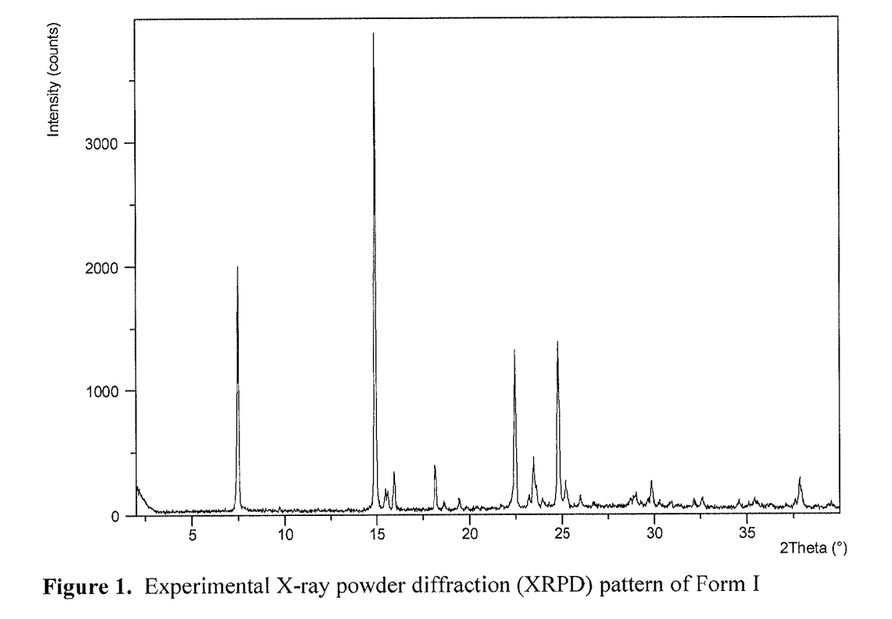
FIG. 1. Presented in FIG. 1 is the experimental X-ray powder diffraction (XRPD) pattern of Form I of tenofovir.

One embodiment provides a crystal form, Form I, of a compound:

which is characterized by a X-ray powder diffraction (XRPD) pattern comprising peaks expressed in degrees (±0.2 degree) of two theta angle of 7.5, 15.0, 22.5 and 24.8 obtained using $CuK\alpha_1$ X-ray (wavelength=1.5406 Angstroms). In another embodiment, the XRPD further comprises a peak at 18.2. In another embodiment, the peaks are selected from the group consisting of at least 4, 5, 6, 7, 8, 9, 10 of the following: 7.5, 15.0, 15.5, 16.0, 18.2, 18.6, 19.4, 22.5, 23.4, 24.8, 25.2, 26.0, 29.0, 29.9, 34.6, 35.4 and 37.8. Preferably, the peaks are selected from the group consisting of at least 4, 5, 6, 7, 8, 9, 10 of the following: 7.5087, 14.9524, 15.5379, 15.9647, 18.1591, 18.6251, 19.4367, 22.4612, 23.452, 24.7844, 25.2111, 26.0309, 28.9775, 29.8565 34.5638, 35.36 and 37.809. In another embodiment, the compound has an XRPD substantially as shown in FIG. 1. In another embodiment, the crystal form of the compound has an XRPD substantially as shown in Table 1. In another embodiment, the crystal form of the compound is characterized by a differential scanning calorimetry (DSC) thermogram comprising an endothermic event with peak maxima at about 98° C.

Figure 2:
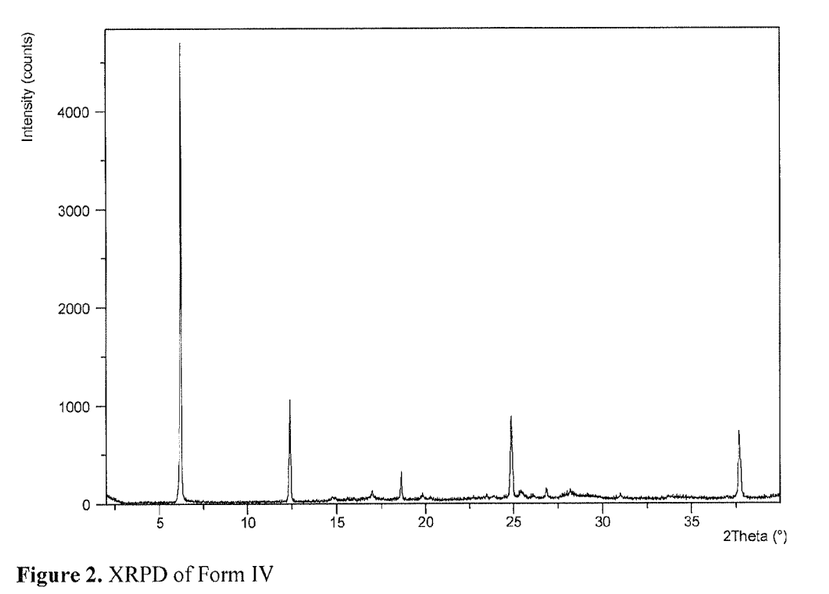
FIG. 2. Presented in FIG. 2 is the XRPD of Form IV of tenofovir.

Another embodiment provides a crystal form, Form IV, of a compound:

which is characterized by a X-ray powder diffraction (XRPD) pattern comprising peaks expressed in degrees (±0.2 degree) of two theta angle of 6.2, 12.4, 18.6, 24.9 and 37.7 obtained using $CuK\alpha_1$ X-ray (wavelength=1.5406 Angstroms). In another embodiment, the XRPD further comprises peaks at 26.8, 17.0 and/or 25.4. In another embodiment, the crystal form is characterized by a X-ray powder diffraction (XRPD) pattern comprising peaks expressed in degrees (±0.2 degree) of two theta angle of 6.2, 12.4, 18.6, 24.7 and 37.7 obtained using $CuK\alpha_1$ X-ray (wavelength=1.5406 Angstroms). In another embodiment, the XRPD further comprises peaks at 26.9, 17.0 and/or 25.4. In another embodiment, the peaks are selected from the group of at least 4, 5, 6, 7, 8, 9, 10 of the following: 6.2, 12.4, 14.8, 17.0, 18.6, 19.8, 24.9, 25.4, 26.8, 28.2, 31.1 and 37.7. Preferably, the peaks are selected from the group of at least 4, 5, 6, 7, 8, 9, 10 of the following: 6.2365, 12.4067, 14.8095, 16.9941, 18.6442, 19.8337, 24.8815, 25.4475, 26.8502, 28.1923, 31.064 and 37.6634. In another embodiment, the crystal form of the compound has an XRPD substantially as shown in FIG. 2. In another embodiment, the crystal form of the compound has an XRPD substantially as shown in Table 3.

Figure 3:
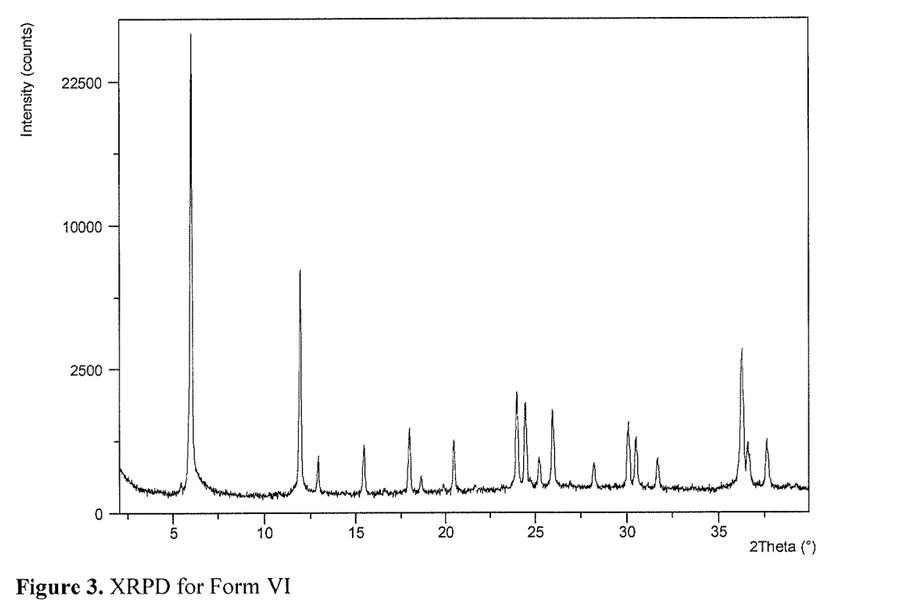
FIG. 3. Presented in FIG. 3 is the XRPD of Form VI of tenofovir.

Another embodiment provides a crystal form, Form VI, of a compound:

which is characterized by a X-ray powder diffraction (XRPD) pattern comprising peaks expressed in degrees (±0.2 degree) of two theta angle of 6.0, 12.0, 24.0, 24.5 and 37.6 obtained using $CuK\alpha_1$ X-ray (wavelength=1.5406 Angstroms). In another embodiment, the XRPD further comprises a peak at 25.9 and/or 30.1. In another embodiment, the peaks are selected from the group consisting of at least 4, 5, 6, 7, 8, 9, 10 of the following: 6.0, 12.0, 12.9, 15.5, 18.0, 18.6, 20.5, 24.0, 24.5, 25.2, 25.9, 28.2, 30.1, 30.5, 31.7, 36.2, 36.6 and 37.6. Preferably, the peaks are selected from the group of at least 4, 5, 6, 7, 8, 9, 10 of the following: 6.0347, 11.9838, 12.9337, 15.4655, 17.9625, 18.6111, 20.4571, 23.9829, 24.4833, 25.2223, 25.9265, 28.1886, 30.0857, 30.4862, 31.6722, 36.2157, 36.6091 and 37.6287. In another embodiment, the crystal form of the compound has an XRPD substantially as shown in FIG. 3. In another embodiment, the crystal form of the compound has an XRPD substantially as shown in Table 2.

Figure 4:
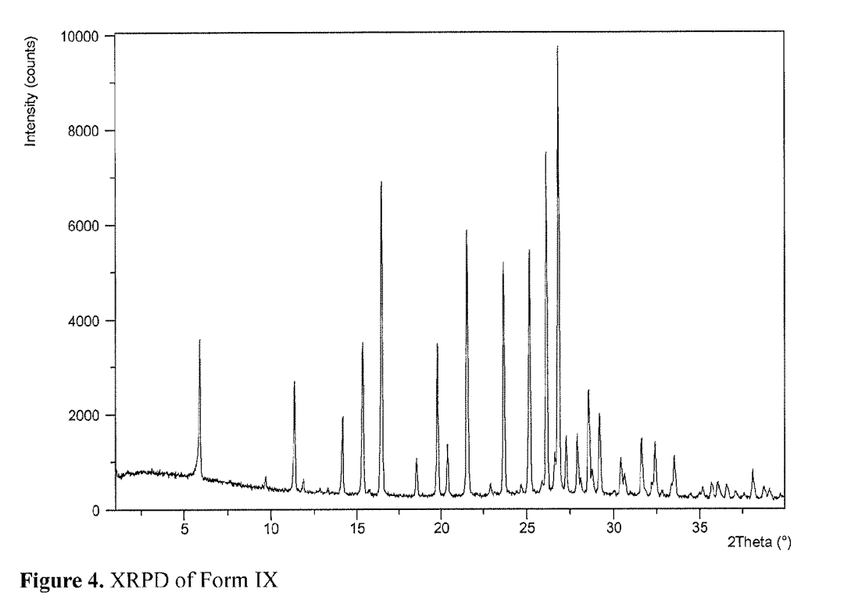
FIG. 4. Presented in FIG. 4 is the XRPD of Form IX of tenofovir.

Another embodiment provides a crystal form, Form IX, of:

which is characterized by a X-ray powder diffraction (XRPD) comprising peaks expressed in degrees (±0.2 degree) of two theta angle of 5.9, 11.3, 16.5, 21.5, 26.1 and 26.8 obtained using CuKα$_1$ X-ray (wavelength=1.5406 Angstroms). In another embodiment, the XRPD further comprises peaks at 14.2, 18.5, 19.8, 20.4, 23.7, 25.1, 26.6, 27.2, 27.9, 28.6 and/or 29.2. Alternatively, in another embodiment, the XRPD further comprises peaks at 14.2, 18.5, 19.8, 20.4, 23.7, 25.1, 26.6, 27.3, 27.9, 28.6 and/or 29.2. In another embodiment, the peaks are selected from the group of at least 4, 5, 6, 7, 8, 9, 10 of the following: 5.9, 11.3, 14.2, 15.4, 16.5, 18.5, 19.8, 20.4, 21.5, 23.7, 25.1, 26.1, 26.6, 26.8, 27.2, 27.9, 28.6, 29.2, 30.4, 31.6, 32.0, 32.4, 33.5, 35.7, 36.0, 36.6, 38.1 and 38.7. Preferably, the peaks are selected from the group of at least 4, 5, 6, 7, 8, 9, 10 of the following: 5.9221, 11.3775, 14.1711, 15.3629, 16.4974, 18.5451, 19.7863, 20.372, 21.5278, 23.6648, 25.1452, 26.1105, 26.5699, 26.7991, 27.2518, 27.9089, 28.5664, 29.181, 30.4312, 31.6126, 32.0314, 32.3945, 33.5187, 35.7008, 36.0498, 36.5879, 38.0934 and 38.7407. In another embodiment, the crystal form of the compound has an XRPD substantially as shown in FIG. 4. In another embodiment, the crystal form of the compound has an XRPD substantially as shown in Table 4.

Another embodiment provides a composition comprising multiple crystalline forms as described herein, specifically Form I and Form IV; Form I and Form VI; Form I and Form IX; Form I, Form IV and Form VI; Form I, Form IV and Form IX; Form I, Form VI and Form IX; Form IV and Form VI; Form IV and Form IX; Form VI and Form IX; Form IV, Form VI and Form IX; and Form I, Form IV, Form VI and Form IX.

Another embodiment provides a composition comprising any one of Material III, Material XIV, Material XVI, Material XVIII and Material XIX and/or any combination thereof.

Another embodiment provides a process for the manufacture of tenofovir disoproxil (TD) comprising converting the crystal form of the compound as described herein to TD. In another embodiment, the reacting step comprises contacting the crystal form of the compound as described herein with triethyl amine (TEA) to form a TEA salt. In another embodiment, the process comprises reacting the crystal form of the compound as described herein with an activated isopropyl ethyl carbonate to form the TD compound. For instance, the process may further comprise reacting the TEA salt with an activated isopropyl ethyl carbonate to form TD. Another embodiment provides further contacting TD with fumaric acid to form tenofovir disoproxil fumarate (TDF). In another embodiment, the crystal form improves processing or manufacturing. In another embodiment, the crystal form improves filterability.

Another embodiment provides a process for the manufacture of tenofovir alafenamide (TAF) comprising converting the crystal form as described herein to form TAF. For instance, the process may comprise reacting a crystal form as described herein with a phenylating agent and an aminating reagent to form TAF. In one embodiment, the crystal form as described herein is contacted with a solvent and reacted with a phenylating agent and an aminating reagent to form TAF. In another embodiment, the phenylating agent comprises triphenoxyphosphine. In another embodiment, the aminating reagent comprises isopropyl 2-aminopropanoate. Another embodiment further comprises the step of contacting TAF with fumaric acid to form TAF fumarate or TAF hemifumarate.

Another embodiment provides a process for the preparation of any of the forms described herein. In one embodiment, the process involves crystallizing PMPA. The process steps are described in more detail in the Examples. Another embodiment provides a product produced by the process of crystallization.

Another embodiment provides a method for treating or preventing a viral infection in a human, comprising administering to the human a crystal form as described herein. More particularly, the viral infection is human immunodeficiency virus (HIV). Alternatively, the viral infection is hepatitis B virus (HBV).

Another embodiment provides a crystal form as described herein for use in therapy. For instance, one embodiment provides a crystal form as described herein for use in a method of treating or preventing a viral infection. Preferably, the viral infection is human immunodeficiency virus (HIV). Alternatively, the viral infection may be hepatitis B virus (HBV).

Another embodiment provides a pharmaceutical composition which comprises the crystal form as described herein. More particularly, the composition further comprises a pharmaceutically acceptable carrier or excipient.

These embodiments and others are further described in the following description.

DETAILED DESCRIPTION OF THE INVENTION

Tenofovir or (R)-9-[2-(phosphonomethoxy) propyl]adenine (PMPA), has the following structure:

Solid state characterization of tenofovir conducted using TGA, DSC, VT XRPD and DVS identified a number of unique XRPD patterns. Further analysis identified forms claimed herein, which are of particular interest because of their favorable shapes and stability for improvement of processing, such as through increased filtration rates.

DEFINITIONS

As referred to in the present application, "anhydrous" refers to a form that does not contain substantial amounts of water. The water content can be determined by methods known in the art including, for example, Karl Fischer titrations. One example of anhydrous form comprises at most about 1% by weight water, or at most about 0.5% by weight water, or at most about 0.1% by weight water.

As referred to in the present application, "stable" means that at least about 90% by weight, or at least about 95% by weight, or at least about 99% by weight of the compound (e.g. PMPA) remains unchanged after storage under the indicated conditions for the indicated time.

"Aminating agent" refers to reagent(s) capable of adding an amino group, such as isopropyl 2-aminopropanoate, to a compound. One example of an aminating agent for PMPA is first activation of a hydroxy substituent with sulfonyl chloride ($SOCl_2$), followed by reaction with the amino group, specifically isopropyl 2-aminopropanoate in an organic aprotic solvent mixture, such as toluene, methylene chloride and THF.

The term "converting" refers to reacting a starting material or intermediate with at least one reagent to form a product. A converting step may include one or more steps to arrive at the final specified product.

The term "crystallizing" refers to the process of formation of a crystalline form from an amorphous form or from a discrete crystal form (i.e. interconversion of crystalline forms).

"DSC" means differential scanning calorimetry.

When referring to a composition comprising a unique pattern, the term "material" refers to a singular form or mixture of crystalline and/or amorphous forms.

"Phenylating agent" refers to reagent(s) capable of adding a phenyl substituent to a compound. An example of a phenylating agent of PMPA is $P(OPh)_3$ or triphenoxyphosphine in conjunction with 4-dimethylaminopyridine (DMAP) and a base, such as triethylamine (TEA).

"PXRD" or "XRPD" used interchangeably refer to the X-ray powder diffraction pattern of a solid form.

The term "substantially" in reference to an X-ray powder diffraction pattern refers to a spectrum having at least 4, 5, 6, 7, 8, 9, 10, 11, 12, 13, 14 or 15 peaks in common with the referenced pattern; or a pattern having at ±0.2 degree of two theta angle within the referenced peaks.

"Tenofovir" or "PMPA" are used interchangeably herein and refer to the following compound:

having the chemical name, (R)-9-[2-(phosphonomethoxy) propyl]adenine.

"Tenofovir Alafenamide" or "TAF" has the following chemical structure:

"Tenofovir disoproxil" or "TD" has the following chemical structure:

"TDF" refers to tenofovir disoproxil fumarate (i.e. the fumarate salt form of TD).

Seeding is a technique of using a single crystal or more to induce the formation of more crystals from a mixture, solution, or suspension. A seeding amount is the amount of material that, when added to a mixture, solution, or suspension, is able to cause the formation of the desired form of a compound. While in theory, this amount can be very small, in practice, a larger amount is used. This amount can be any amount that can be reasonably handled and is sufficient to cause the formation of the desired form of a compound. As a non-limiting example, amounts of 0.0001% to 50% wt/wt of the seeding compound based on a reference compound can be used as a seeding amount.

The term "C" when used in reference to temperature means centigrade or Celsius.

"Ambient temperature" is the air temperature surrounding an object. It is the temperature inside a room, which generally is from 15 to 25 degrees centigrade.

Reflux is a technique used in chemistry to apply energy to reactions over an extended period of time. For this technique, a liquid reaction mixture is placed in a vessel open only at the top. This vessel is connected to a vertical condenser, such that any vapors given off are cooled back to liquid, and fall back into the reaction vessel. The vessel is then heated vigorously for the course of the reaction. The advantage of this technique is that it can be left for a long period of time without the need to add more solvent or fear of the reaction vessel boiling dry. In addition because a given solvent will always boil at a certain temperature, the reaction will proceed at the same temperature. Because different solvents boil at different temperatures, by careful choice of solvent, the temperature of the reaction can be controlled. "Reflux temperature" as used herein refers to the temperature at which a particular solvent boils during the reflux technique. For example, 2-propanol has a boiling point of 82° C.; methanol has a boiling point of 65° C. at sea level.

"Therapeutically effective amount" refers to that amount of the compound being administered which will prevent a condition, or will relieve to some extent one or more of the symptoms of the disorder being treated. Pharmaceutical compositions suitable for use herein include compositions wherein the active ingredients are contained in an amount sufficient to achieve the intended purpose. Determination of a therapeutically effective amount is well within the capability of those skilled in the art, especially in light of the detailed disclosure provided herein.

In practice, the amount of the compound to be administered ranges from about 0.001 to 100 mg per kg of body weight, such total dose being given at one time or in divided doses. It may be administered alone or in combination with one or more other drugs. Generally, it will be administered as a formulation in association with one or more pharmaceutically acceptable excipients. The choice of excipient will to a large extent depend on factors such as the particular mode of administration, the effect of the excipient on solubility and stability, and the nature of the dosage form.

Pharmaceutical compositions suitable for the delivery of compounds described herein and methods for their preparation will be readily apparent to those skilled in the art. Such compositions and methods for their preparation may be found, for example, in *Remington's Pharmaceutical Sciences*, 19th Edition (Mack Publishing Company, 1995).

In the following description of the examples, specific embodiments in which the invention may be practiced are described. These embodiments are described in sufficient detail to enable those skilled in the art to practice the invention. Other embodiments may be utilized, and logical and other changes may be made without departing from the scope of the invention. The following detailed description is, therefore, not to be taken in a limiting sense, and the scope of the invention is defined only by the appended claims, along with the full scope of equivalents to which such claims are entitled.

EXAMPLES

Example 1

Preparation and Characterization of Form I

Form I is a monohydrate obtained from crystallization through the following process. The pH of the reaction mixture of (PMPA, water, DMF and HBr) was adjusted to 1.3 using aqueous NaOH solution at about 15 to 30° C. The PMPA solution was maintained at about 15 to 30° C. At this point the mixture may be seeded with crystals to enhance formation, but was not necessary. Aqueous NaOH was added over about 2 to 4 hours at about 15 to 30° C. to obtain a pH of about 1.7. The slurry then rested at about 15 to 30° C. for about 1 h. Aqueous NaOH was added at about 15 to 30° C. to pH of about 2.8 at about 15 to 30° C. over about 4 h. The slurry was then cooled to about 0 to 6° C. and let sit for about 3 h. The mixture was then filtered and charged: 4.5× water at about 0 to 6° C. for top wash; 2× acetone at about 15 to 30° C. and agitated for about 30 min before filtration, then charged 2× acetone at about 15 to 30° C. for top wash. The crystals were dried at 21° C. to 70° C. for about 24 hours.

Crystals of Form I were obtained. The PXRD is shown in FIG. 1 under the following the experimental settings: 45 kV, 40 mA, Kα1=1.5406 Å, scan range 2 to 40°, step size 0.0167°, counting time: 15.875 s.

Prominent peaks were selected from observed peaks by identifying substantially non-overlapping, low-angle peaks with strong intensity. The prominent peaks of PMPA Form I include: 7.5, 15.0, 18.2, 22.5, 24.8±0.2° 2 Theta. The observed peaks of PMPA Form I are shown in Table 1.

TABLE 1

Observed peaks in the XRPD pattern of PMPA Form I

| No. | Pos. [° 2 Th.] | Rel. Int. [%] |
|---|---|---|
| 1 | 7.5 | 49.83 |
| 2 | 15.0 | 100 |
| 3 | 15.5 | 2.91 |
| 4 | 16.0 | 6.89 |
| 5 | 18.2 | 8.87 |
| 6 | 18.6 | 1.12 |
| 7 | 19.4 | 1.67 |
| 8 | 22.5 | 32.59 |
| 9 | 23.4 | 8.77 |
| 10 | 24.8 | 34.1 |
| 11 | 25.2 | 5.25 |
| 12 | 26.0 | 1.67 |
| 13 | 29.0 | 1.93 |
| 14 | 29.9 | 5.05 |
| 15 | 34.6 | 1.12 |
| 16 | 35.4 | 0.93 |
| 17 | 37.8 | 5.67 |

Thermogravimetric analysis (TGA) data was obtained using 2.01 mg PMPA Form I and was heated at a rate of 10° C./min over the range of 25 to 350° C. The solids lost about 6.1% water below 100° C., and the loss is very close to the theoretical water content of 5.9% for PMPA monohydrate. The TGA data of Form I show that it dehydrates at about 50° C. under nitrogen purge.

A differential scanning calorimetry (DSC) analysis was conducted using 2.0 mg of PMPA Form I sample and heating at a rate of 10° C./min over the range of 25 to 300° C. DSC thermogram showed an endothermic event with peak maxima at about 98° C., corresponding to water loss.

Comparison of XRPD patterns at 70, 80, and 90° C. during the heating period showed that transition from monohydrate (Form I) to an anhydrous form occurred around 80° C.

Example 2

Preparation and Characterization of Form VI

Form VI was obtained from the process as follows. The pH of PMPA reaction mixture was adjusted to about 0.65 to 0.85 using aqueous NaOH solution or HBr at about 19 to 25° C. The PMPA solution was cooled to about 0 to 6° C. and aged for about 1-2 h for self crystallization. The resultant slurry was left for about 2 h to form a seed bed. Aqueous NaOH was added at about 0 to 6° C. to a pH of about 1.1 over about 3 to 4 h and the slurry was left to rest at about 0 to 6° C. for about 2 h. Aqueous NaOH was added at about 0 to 6° C. to pH of about 2.8 over about 4 h. The slurry was then left to rest at about 0 to 6° C. for about 3 h and then filtered to separate solids.

Alternatively, Form VI is obtained by dissolving 400 mg Form I in 20 ml water at about 75° C., cooled to about 0 to 6° C. without stirring.

The XRPD pattern of PMPA Form VI (FIG. 3) was obtained in the experimental setting as follows: 45 kV, 40 mA, Kα1=1.5406 Å, scan range 2 to 40°, step size 0.0167°, counting time: 15.875 s.

The list of prominent peaks of PMPA Form VI include: 6.0, 12.0, 24.0, 24.5, 37.6±0.2° 2 Theta. The list of observed peaks of PMPA Form VI is shown in Table 2.

TABLE 2

Observed peaks in the XRPD pattern of PMPA Form VI

| No. | Pos. [° 2 Th.] | Rel. Int. [%] |
|---|---|---|
| 1 | 6.0 | 100 |
| 2 | 12.0 | 25.45 |
| 3 | 12.9 | 1.19 |
| 4 | 15.5 | 1.7 |
| 5 | 18.0 | 2.86 |
| 6 | 18.6 | 0.34 |
| 7 | 20.5 | 2.08 |
| 8 | 24.0 | 5.92 |
| 9 | 24.5 | 4.92 |
| 1d | 25.2 | 0.98 |
| 11 | 25.9 | 3.98 |
| 12 | 28.2 | 0.78 |
| 13 | 30.1 | 3.11 |
| 14 | 30.5 | 1.86 |
| 15 | 31.7 | 0.87 |
| 16 | 36.2 | 9.12 |
| 17 | 36.6 | 1.7 |
| 18 | 37.6 | 1.86 |

TGA data was obtained using 3.88 mg PMPA Form VI at a heating rate of 10° C./min over the range of about 30 to 250° C. The solids lost about 24.7% water at about 100° C., and the loss was close to the theoretical water content of about 23.9% for PMPA pentahydrate.

Example 3

Preparation and Characterization of Form IV

Form IV was obtained by keeping Form VI in water at ambient temperature for 3 weeks. XRPD analysis show the sample did not change when kept in a sealed vial at ambient temperature.

The XRPD pattern (FIG. 2) of PMPA Form IV was obtained under the following the experimental settings: 45 kV, 40 mA, Kα1=1.5406 Å, scan range 2 to 40°, step size 0.0167°, counting time: 15.875 s.

The prominent peaks of PMPA Form IV include: 6.2, 12.4, 18.6, 24.9, 37.7±0.2° 2 Theta. The observed peaks of PMPA Form IV are shown in Table 3.

TABLE 3

Observed peaks in the XRPD pattern of PMPA Form IV

| No. | Pos. [° 2 Th.] | Rel. Int. [%] |
|---|---|---|
| 1 | 6.2 | 100 |
| 2 | 12.4 | 23.04 |
| 3 | 14.8 | 0.57 |
| 4 | 17.0 | 1.72 |
| 5 | 18.6 | 5.9 |
| 6 | 19.8 | 0.8 |
| 7 | 24.9 | 18.24 |
| 8 | 25.4 | 1.34 |
| 9 | 26.8 | 1.81 |
| 10 | 28.2 | 0.81 |
| 11 | 31.1 | 0.45 |
| 12 | 37.7 | 13.5 |

TGA data was obtained using 6.63 mg PMPA Form IV (dried by filter paper) at a heating rate of 10° C./min over the range of 30 to 250° C. The solids lost about 28.6% water at about 100° C. The weight loss is close to the theoretical water content of 27.3% for PMPA hexahydrate.

Example 4

Preparation and Characterization of Form IX

A solution of 51 mg of PMPA in 1 mL water at 2 to 8° C. was mixed for two weeks and then vacuum filtered while cold. The wet solid was analyzed by XRPD to be Form IX.

Subsequent production of Form IX occurred by use of PMPA (0.5 g) Form I solids stirred in 10 ml water between 2° C. and 8° C. in the presence of Form IX seeds. After about 5 days, an opaque white suspension resulted. The slurry was filtered under vacuum, and solids were collected. The crystals appeared to be plates/rods.

A high resolution XRPD pattern of Form IX (FIG. 4) was collected with a PANalytical X'Pert PRO MPD diffractometer using an incident beam of Cu radiation. A specimen of the sample was sandwiched between 3-μm-thick films and analyzed in transmission geometry.

The prominent peaks of PMPA Form IX include: 5.9, 11.3, 16.5, 21.5, 26.1, 26.8±0.2° 2 Theta. The list of observed peaks is shown in Table 4.

TABLE 4

Observed peaks in the XRPD pattern of PMPA Form IX

| No. | Pos. [° 2 Th.] | Rel. Int. [%] |
|---|---|---|
| 1 | 5.9 | 31.87 |
| 2 | 11.3 | 24.78 |
| 3 | 14.2 | 17.44 |
| 4 | 15.4 | 34.56 |
| 5 | 16.5 | 71.15 |
| 6 | 18.5 | 8.02 |
| 7 | 19.8 | 34.86 |
| 8 | 20.4 | 11.71 |
| 9 | 21.5 | 61.09 |
| 10 | 23.7 | 53.51 |
| 11 | 25.1 | 54.43 |
| 12 | 26.1 | 77.04 |
| 13 | 26.6 | 8.13 |
| 14 | 26.8 | 100 |
| 15 | 27.2 | 12.3 |
| 16 | 27.9 | 13.02 |
| 17 | 28.6 | 23.86 |
| 18 | 29.2 | 17.2 |
| 19 | 30.4 | 8.12 |
| 20 | 31.6 | 13.07 |
| 21 | 32.0 | 0.26 |

TABLE 4-continued

Observed peaks in the XRPD pattern of PMPA Form IX

| No. | Pos. [° 2 Th.] | Rel. Int. [%] |
|---|---|---|
| 22 | 32.4 | 11.22 |
| 23 | 33.5 | 9.33 |
| 24 | 35.7 | 3.18 |
| 25 | 36.0 | 3.24 |
| 26 | 36.6 | 2.63 |
| 27 | 38.1 | 5.68 |
| 28 | 38.7 | 2.43 |

The high resolution XRPD pattern of PMPA Form IX was successfully indexed. The unit cell parameters and calculated volume at ambient temperature, derived from indexing, are: a=6.817 Å, b=29.764 Å, c=18.222 Å, α=90°, β=90°, γ=90°, V=3697.3 Å$^3$.

TGA data was obtained using 12.27 mg PMPA Form IX at a heating rate of 10° C./min over the range of 30 to 350° C. PMPA Form IX exhibits weight loss of about 30.1% at about 100° C. The weight loss is close to the theoretical water content of 30.5% for PMPA heptahydrate.

DSC data was obtained using 2.7 mg PMPA Form IX at a heating rate of 10° C./min over the range of 30 to 250° C. The sample was placed in an aluminum pan with a pierced lid. PMPA Form IX shows endothermic events with peak maxima at 0° C., 57° C., 103° C. and 127° C.

Example 5

Other Unique XRPD Patterns/Materials Observed

Figure 5:
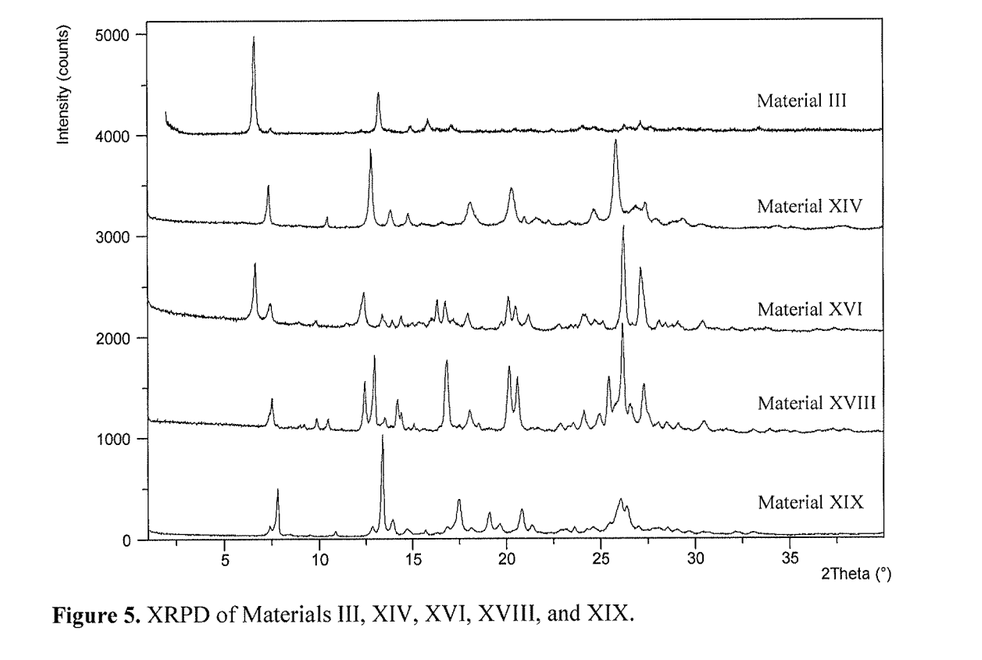
FIG. 5. Presented in FIG. 5 is the XRPD of Materials III, XIV, XVI, XVIII, and XIX.

Other XRPD patterns of PMPA (FIG. 5) were observed during the investigations. The methods used to obtain those patterns/materials are listed in Table 5.

TABLE 5

Other unique XRPD patterns

| Designation | Description/Composition | Preparation Conditions |
|---|---|---|
| Material III | Low hydrate (in mixture with Form I) | Partially dehydrated from Form VI at RT |
| Material XIV | Low hydrate (in mixtures with Form I) | Vacuum drying of Form IX at about 21 to 63° C. |
| Material XVI | Trihydrate (possibly in mixtures with Form I and Form IX) | (1) Lyophilization in water (2) Form IX in humidity chamber at about 22% and about 97% RH |
| Material XVIII | Low hydrate (in mixture containing Material XIV, Material XVI, Form I, et. al.) | Drying Form IX over P$_2$O$_5$ |
| Material XIX | Contains residual acetone, may be hydrates | Form IX slurry in acetone, then vacuum dried at about 40° C. |

Example 6

Process Improvements with Crystalline Forms

The TDF manufacturing process has variable filtration times for PMPA on lab scale and on plant scale. The variation in filtration time was caused by different crystal habits (associated with Form I and Form VI) during the crystallization process. Samples of production batches of PMPA were filtered on lab scale equipment to evaluate the filtration times.

The filtration time for batch 1 was significantly shorter than the filtration times for batches 2 and 3 (approximately 3-fold). The slurries for these batches were observed under a polarized light microscope (PLM). Batch 1 consisted of a mixture of fine needles (Form I) and plates (Form VI), while the other two batches only contains needles (Form I). This finding suggested that Form I and VI could be formed during PMPA crystallizations and the presence of a sufficient amount of Form VI gave an improved filtration time.

A demonstration batch (146 kg starting material input) was conducted to produce Form VI. It should be noted that although Form VI was produced during crystallization, the final isolated form is Form I after drying.

The filtration results are shown in Table 6, together with the averages of the 40 batches at the contract manufacturing organization. The filtration of the demonstration batch was completed at approximately ⅓ of the average filtration time of the 40 batches at the contract manufacturing organization.

TABLE 6

Comparison of the filtration time in the plant demonstration

| Batch | Filtration Time (h) | Form before filtration |
|---|---|---|
| 2431-HC-1P | 11 | Form VI |
| Batch Averages | 33 | Form I mostly |

CONCLUSION

The use of crystal forms, as described above, provides a number of advantages including improvement of processing and manufacturing, specifically filtration rates. The improvement in filtration rate has been demonstrated on manufacturing scale. As a result of the improved crystal form, the filtration time was approximately ⅓ of the filtration time of a previous crystal form. An improved filtration shortens the cycle time of the process which has a positive impact on operating cost.

The invention claimed is:

1. A crystal form, Form I, of a compound:

which is characterized by a X-ray powder diffraction (XRPD) pattern comprising peaks expressed in degrees of two theta angle of 7.5±0.2, 15.0±0.2, 22.5±0.2 and 24.8±0.2 obtained using CuKα$_1$ X-ray.

2. The crystal form of claim 1, having an XRPD pattern having at least 5 peaks in common with the pattern as shown in FIG. 1 wherein the at least 5 peaks in common are at ±0.2 degree of two theta angle within the peaks of FIG. 1.

3. The crystal form of claim 1, having an XRPD pattern with peaks at ±0.2 degree of two theta angle within the peaks shown in Table 1:

TABLE 1

| No. | Pos. [° 2 Th.] | Rel. Int. [%] |
|---|---|---|
| 1 | 7.5 | 49.83 |
| 2 | 15.0 | 100 |
| 3 | 15.5 | 2.91 |
| 4 | 16.0 | 6.89 |
| 5 | 18.2 | 8.87 |
| 6 | 18.6 | 1.12 |
| 7 | 19.4 | 1.67 |
| 8 | 22.5 | 32.59 |
| 9 | 23.4 | 8.77 |
| 10 | 24.8 | 34.1 |
| 11 | 25.2 | 5.25 |
| 12 | 26.0 | 1.67 |
| 13 | 29.0 | 1.93 |
| 14 | 29.9 | 5.05 |
| 15 | 34.6 | 1.12 |
| 16 | 35.4 | 0.93 |
| 17 | 37.8 | 5.67. |

4. The crystal form of claim 1, characterized by a differential scanning calorimetry (DSC) thermogram comprising an endothermic event with peak maxima at 98° C.

5. A crystal form, Form IV, of a compound:

which is characterized by a X-ray powder diffraction (XRPD) pattern comprising peaks expressed in degrees of two theta angle of 6.2±0.2, 12.4±0.2, 18.6±0.2, 24.9±0.2 and 37.7±0.2 obtained using CuKα₁ X-ray.

6. The crystal form of claim 5, having an XRPD pattern having at least 5 peaks in common with the pattern as shown in FIG. 2 wherein the at least 5 peaks in common are at ±0.2 degree of two theta angle within the peaks of FIG. 2.

7. The crystal form of claim 5, having an XRPD pattern with peaks at ±0.2 degree of two theta angle within the peaks shown in Table 3:

TABLE 3

| No. | Pos. [° 2 Th.] | Rel. Int. [%] |
|---|---|---|
| 1 | 6.2 | 100 |
| 2 | 12.4 | 23.04 |
| 3 | 14.8 | 0.57 |
| 4 | 17.0 | 1.72 |
| 5 | 18.6 | 5.9 |
| 6 | 19.8 | 0.8 |
| 7 | 24.9 | 18.24 |
| 8 | 25.4 | 1.34 |
| 9 | 26.8 | 1.81 |
| 10 | 28.2 | 0.81 |
| 11 | 31.1 | 0.45 |
| 12 | 37.7 | 13.5. |

8. A crystal form, Form VI, of a compound:

which is characterized by a X-ray powder diffraction (XRPD) pattern comprising peaks expressed in degrees of two theta angle of 6.0±0.2, 12.0±0.2, 24.0±0.2, 24.5±0.2 and 37.6±0.2 obtained using CuKα₁ X-ray.

9. The crystal form of claim 8, having an XRPD pattern having at least 5 peaks in common with the pattern as shown in FIG. 3 wherein the at least 5 peaks in common are at ±0.2 degree of two theta angle within the peaks of FIG. 3.

10. The crystal form of claim 8, having an XRPD pattern with peaks at ±0.2 degree of two theta angle within the peaks shown in Table 2:

TABLE 2

| No. | Pos. [° 2 Th.] | Rel. Int. [%] |
|---|---|---|
| 1 | 6.0 | 100 |
| 2 | 12.0 | 25.45 |
| 3 | 12.9 | 1.19 |
| 4 | 15.5 | 1.7 |
| 5 | 18.0 | 2.86 |
| 6 | 18.6 | 0.34 |
| 7 | 20.5 | 2.08 |
| 8 | 24.0 | 5.92 |
| 9 | 24.5 | 4.92 |
| 10 | 25.2 | 0.98 |
| 11 | 25.9 | 3.98 |
| 12 | 28.2 | 0.78 |
| 13 | 30.1 | 3.11 |
| 14 | 30.5 | 1.86 |
| 15 | 31.7 | 0.87 |
| 16 | 36.2 | 9.12 |
| 17 | 36.6 | 1.7 |
| 18 | 37.6 | 1.86. |

11. A crystal form, Form IX, of a compound:

which is characterized by a X-ray powder diffraction (XRPD) pattern comprising peaks expressed in degrees of two theta angle of 5.9±0.2, 11.3±0.2, 16.5±0.2, 21.5±0.2, 26.1±0.2 and 26.8±0.2 obtained using CuKα₁ X-ray.

12. The crystal form of claim 11, having an XRPD pattern having at least 5 peaks in common with the pattern as shown in FIG. 4 wherein the at least 5 peaks in common are at ±0.2 degree of two theta angle within the peaks of FIG. 4.

13. The crystal form of claim 11, having an XRPD pattern with peaks at ±0.2 degree of two theta angle within the peaks shown in Table 4:

TABLE 4

| No. | Pos. [° 2 Th.] | Rel. Int. [%] |
|---|---|---|
| 1 | 5.9 | 31.87 |
| 2 | 11.3 | 24.78 |
| 3 | 14.2 | 17.44 |
| 4 | 15.4 | 34.56 |
| 5 | 16.5 | 71.15 |
| 6 | 18.5 | 8.02 |
| 7 | 19.8 | 34.86 |
| 8 | 20.4 | 11.71 |
| 9 | 21.5 | 61.09 |
| 10 | 23.7 | 53.51 |
| 11 | 25.1 | 54.43 |
| 12 | 26.1 | 77.04 |
| 13 | 26.6 | 8.13 |
| 14 | 26.8 | 100 |
| 15 | 27.2 | 12.3 |
| 16 | 27.9 | 13.02 |
| 17 | 28.6 | 23.86 |
| 18 | 29.2 | 17.2 |
| 19 | 30.4 | 8.12 |
| 20 | 31.6 | 13.07 |
| 21 | 32.0 | 0.26 |
| 22 | 32.4 | 11.22 |
| 23 | 33.5 | 9.33 |
| 24 | 35.7 | 3.18 |
| 25 | 36.0 | 3.24 |
| 26 | 36.6 | 2.63 |
| 27 | 38.1 | 5.68 |
| 28 | 38.7 | 2.43. |

14. A composition comprising a crystal form Form I and a crystal form Form IV of a compound:

wherein:
Form I is characterized by a X-ray powder diffraction (XRPD) pattern comprising peaks expressed in degrees of two theta angle of 7.5±0.2, 15.0±0.2, 22.5±0.2 and 24.8±0.2 obtained using CuKα₁ X-ray; and
Form IV is characterized by a X-ray powder diffraction (XRPD) pattern comprising peaks expressed in degrees of two theta angle of 6.2±0.2, 12.4±0.2, 18.6±0.2, 24.9±0.2 and 37.7±0.2 obtained using CuKα₁ X-ray.

15. A composition comprising a crystal form Form I and a crystal form Form VI of a compound:

wherein:
Form I is characterized by a X-ray powder diffraction (XRPD) pattern comprising peaks expressed in degrees of two theta angle of 7.5±0.2, 15.0±0.2, 22.5±0.2 and 24.8±0.2 obtained using CuKα₁ X-ray; and
Form VI is characterized by a X-ray powder diffraction (XRPD) pattern comprising peaks expressed in degrees of two theta angle of 6.0±0.2, 12.0±0.2, 24.0±0.2, 24.5±0.2 and 37.6±0.2 obtained using CuKα₁ X-ray.

16. A composition comprising a crystal form Form I and a crystal form Form IX of a compound:

wherein:
Form I is characterized by a X-ray powder diffraction (XRPD) pattern comprising peaks expressed in degrees of two theta angle of 7.5±0.2, 15.0±0.2, 22.5±0.2 and 24.8±0.2 obtained using CuKα₁ X-ray; and
Form IX is characterized by a X-ray powder diffraction (XRPD) pattern comprising peaks expressed in degrees of two theta angle of 5.9±0.2, 11.3±0.2, 16.5±0.2, 21.5±0.2, 26.1±0.2 and 26.8±0.2 obtained using CuKα₁ X-ray.

17. A pharmaceutical composition comprising the crystal form of claim 1.

18. The composition of claim 17, further comprising a pharmaceutically acceptable carrier or excipient.

* * * * *

UNITED STATES PATENT AND TRADEMARK OFFICE
CERTIFICATE OF CORRECTION

PATENT NO. : 9,487,546 B2
APPLICATION NO. : 14/593556
DATED : November 8, 2016
INVENTOR(S) : Paul Bernard Hurley et al.

It is certified that error appears in the above-identified patent and that said Letters Patent is hereby corrected as shown below:

On the Title Page

Other Publications
Column 2, Line 10, delete "Opion" and insert -- Opinion --

In the Claims

Claim 14, Column 15, Lines 36-45, replace:

With:

Signed and Sealed this
Fourteenth Day of November, 2017

Joseph Matal
*Performing the Functions and Duties of the
Under Secretary of Commerce for Intellectual Property and
Director of the United States Patent and Trademark Office*

CERTIFICATE OF CORRECTION (continued)

Claim 15, Column 16, Lines 5-15, replace:

With:

Claim 16, Column 16, Lines 27-37, replace:

With: